United States Patent
Avakgharagelou

(10) Patent No.: US 6,617,164 B1
(45) Date of Patent: Sep. 9, 2003

(54) METHOD AND APPARATUS FOR PRODUCING STANDARD GASES, CARBON MONOXIDE, AND HYDROGEN FOR DETERMINING ISOTOPE RELATIONSHIPS

(75) Inventor: Hairigh Avakgharagelou, Lilienthal (DE)

(73) Assignee: Finnigan MAT GmbH, Bremen (DE)

( * ) Notice: Subject to any disclaimer, the term of this patent is extended or adjusted under 35 U.S.C. 154(b) by 0 days.

(21) Appl. No.: 09/721,336

(22) Filed: Nov. 22, 2000

(30) Foreign Application Priority Data

Nov. 25, 1999 (DE) .......................... 199 56 632

(51) Int. Cl.[7] .................. G01N 31/00; G01N 24/00; G01N 1/22

(52) U.S. Cl. .................. 436/8; 436/9; 436/134; 436/136; 436/144; 436/155; 436/173; 436/174; 436/181; 422/78; 422/83; 250/281; 250/282; 250/283; 250/288

(58) Field of Search .................. 436/8, 9, 127, 436/133, 134, 136, 144, 161, 173, 174, 181, 182, 155; 422/83, 78; 250/281, 282, 283, 288

(56) References Cited

U.S. PATENT DOCUMENTS

| 3,604,698 | A | * | 9/1971 | Themelis et al. ............ 266/226 |
| 4,517,461 | A | * | 5/1985 | Crandall ...................... 250/281 |
| 4,866,270 | A | * | 9/1989 | Hall et al. ................... 250/282 |
| 4,916,313 | A | * | 4/1990 | Hall et al. ................... 250/282 |
| 5,012,052 | A | * | 4/1991 | Hayes ......................... 250/282 |
| 5,314,827 | A | * | 5/1994 | Schmidt et al. ............. 250/282 |
| 5,766,954 | A | * | 6/1998 | Freedman et al. .......... 436/144 |
| 6,031,228 | A | * | 2/2000 | Abramson ................... 250/281 |

FOREIGN PATENT DOCUMENTS

| DE | 3721671 | 7/1988 |
| EP | 0 306 332 | 3/1989 |
| FR | 2734363 | * 11/1996 |
| GB | 116427 | 1/1966 |
| GB | 2254696 | 10/1992 |

OTHER PUBLICATIONS

Kelly et al. Journal of Mass Spectrometry. vol. 33, 1998, pp. 735–738.*
Koziet. Journal of Mass Spectrometry. vol. 32, 1997, pp. 103–108.*
Gehre et al. Analytical Chemistry. vol. 68, 1996, pp. 4414–4417.*
Saurer, M. et al., "Oxygen Isotope Analysis of Cellulose: An Interlaboratory Comparison", Anal. Chem., 1998, 70, pp. 2074–2080.

* cited by examiner

*Primary Examiner*—Maureen M. Wallenhorst
(74) *Attorney, Agent, or Firm*—Dorsey & Whitney LLP

(57) ABSTRACT

The invention, relates to a method for producing standard gases (CO and $H_2$) for determining the isotope relationships of oxygen and/or hydrogen, in particular during on-line operation, with a sample being decomposed in a (hot) reactor (11) to produce CO and/or $H_2$, and these components being fed to a mass spectrometer (15), and with the mass spectrometer also the gases obtained from the sample. The invention also relates to an apparatus for providing standard gases. The method according to the invention provides for the standard gases in the reactor (11) to be formed by decomposition, and for initial products which are suitable for this purpose to be fed to the reactor.

6 Claims, 4 Drawing Sheets

METHOD AND APPARATUS FOR PRODUCING STANDARD GASES, CARBON MONOXIDE, AND HYDROGEN FOR DETERMINING ISOTOPE RELATIONSHIPS

The invention relates to a method for producing standard gases (CO and $H_2$) for determining the isotope relationships of oxygen and/or hydrogen, in particular during on-line operation, with a sample being decomposed in a (hot) reactor to produce CO and/or $H_2$, and these components being fed to a mass spectrometer, and with the mass spectrometer also being fed with the standard gases for comparison with the gases obtained from the sample. The invention also relates to an apparatus for producing standard gases.

Determination of the isotope composition of hydrogen D/H and oxygen $^{18}O/^{16}O$ in organic (including water) or inorganic samples is of major importance in hydrology, ecology, foodstuffs chemistry, medicine etc. In order to avoid human errors and to achieve accurate measurement from as many samples as possible in a very short time, the method is carried out during so-called on-line operation. In this case, the samples are placed in a crucible and are introduced into a hot reactor (1450° C.) by a so-called auto sampler in accordance with a defined time programme. The reactor contains elementary carbon, and helium flows through it as a carrier gas. The sample is decomposed in the reactor into its constituents, including CO and $H_2$ (assuming these elements were present in the sample). The constituents are then separated from one another in a gas chromatograph, and are analysed successively in a mass spectrometer. An on-line method is described by Saurer et al. in Analytical Chemistry, Vol. 70, No. 10, 1998, pages 2074 to 2080.

The isotope composition of hydrogen and oxygen in the sample is not determined by measuring absolute values. In fact, a comparison is always carried out with so-called standard gases (CO, $H_2$). These standard gases (a defined quantity) must be fed to the mass spectrometer alternately with the constituents obtained from the sample. A number of successive measurements are combined, and are evaluated in order to calculate the isotope composition in the sample relative to the isotope composition in the standard gases. The standard gases are supplied before and after the sample measurement (FIG. 1).

The standard gases are provided in cylinders at a pressure of 200 bar, close to the mass spectrometer. Special precautionary measures are required, since carbon monoxide is extremely toxic, and hydrogen is highly explosive.

The object of the present invention is to provide a method and an apparatus which are safer when used in conjunction with the provision of standard gases.

The method according to the invention is characterized in that the standard gases in the reactor are formed by decomposition, and initial products which are suitable for this purpose are fed to the reactor. It is possible to choose initial products which are safer than CO and $H_2$ and can be decomposed in the reactor into these constituents.

Carbon dioxide ($CO_2$) is advantageously used as an initial product of CO, and/or n-alkanes are used for $H_2$. Carbon dioxide is neither toxic nor explosive. The chosen n-alkanes are preferably those which are less combustible or less explosive, while also being easy to handle, such as propane or butane.

The initial products are decomposed in the reactor to form the standard gases. The latter thus pass, at the latest after the reactor, through the same pipe runs as the constituents obtained from the samples. This reduces fluctuations in the measurement results.

The apparatus according to the invention is naturally particularly suitable for carrying out the method and is characterized by means for feeding initial products for the standard gases into the reactor. As stated above, the standard gases have until now been fed directly to the mass spectrometer. Using the apparatus according to the invention, it is for the first time possible to feed initial products into the reactor to form the standard gases.

The said means for feeding initial products for the standard gases into the reactor advantageously have at least the following components:

a line system, a connection for at least one initial product, a connection for a carrier gas supply, a line leading to the reactor, a storage line (loop) and switching means for feeding the initial product into the storage line at times and for likewise carrying the contents of the storage line away at times, with the aid of the carrier gas, into the reactor.

The switching means are preferably constructed on the principle of a rotary valve, such as may be obtained from, for instance, Valco Instruments Co. Inc. (Houston, Tex.), having at least six connections. The connections are connected to one another by means of a common pipeline ring. By operating the valve, it is possible to connect two connections to one another in each case in a first switch position, and to produce two other connection pairs in each case in a second switch position. In this way, an initial product can be fed to the storage line, while the carrier gas is flowing into the reactor. After switching the valve over, the initial product in the storage line is transported into the reactor by the carrier gas, while the initial product connected to the valve is carried away. Taking account of the volumes of the pipeline and the flow rates of the initial product and carrier gas, an initial product can be fed at specific intervals and in suitable amounts to the reactor by switching over the valve for specific intervals.

Further features of the invention result from the claims. Exemplary embodiments of the invention will be explained in more detail in the following text with reference to the drawings, in which:

The apparatus described in the following text is intended for determining the isotope composition of oxygen from an organic sample. Water or inorganic samples may also be used.

The samples are placed in crucibles, which are not shown, and are inserted into a so-called auto sampler 10. This uses computer control to ensure successive transport of the crucibles into a reactor 11 (in the absence of air), in which the temperature is about 1450° C.

Elementary carbon is arranged in the reactor. In addition, helium flows through the reactor, as a carrier gas, see the reactor supply line 12 and the outlet line 13.

Figure 1:
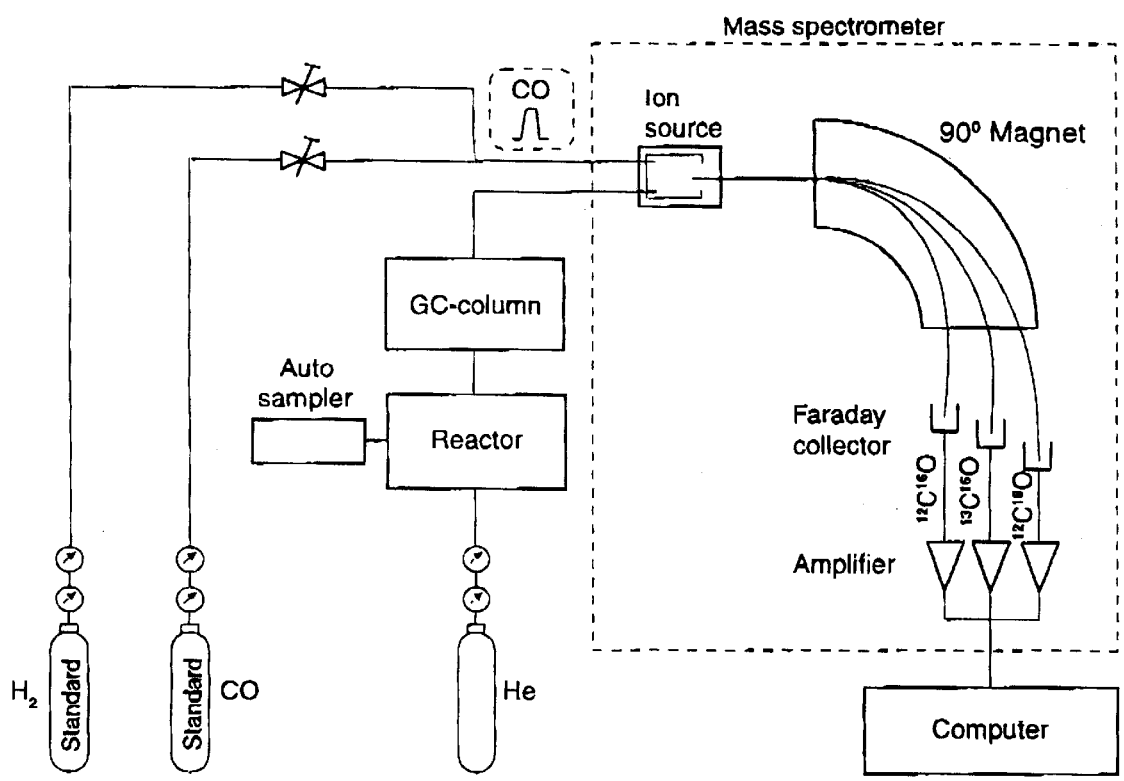
FIG. 1 shows the prior art
Figure 2:
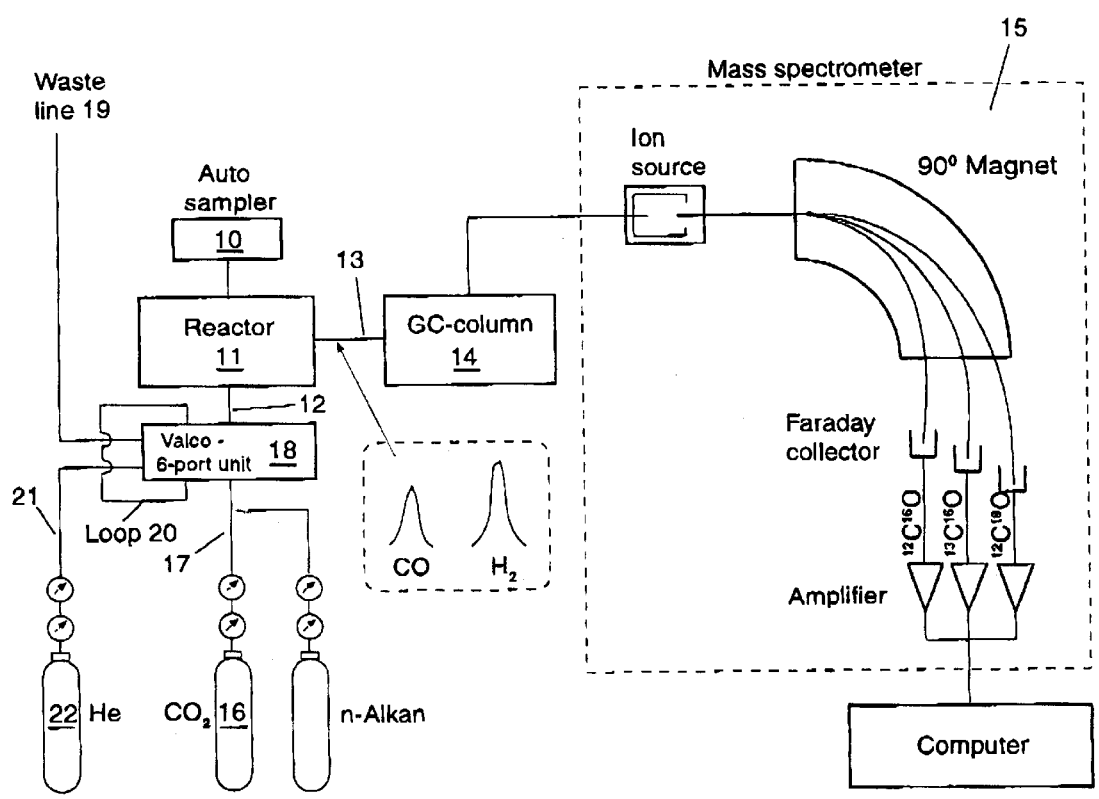
FIG. 2 shows a schematic illustration of a system for isotope determination.

The high temperature in the reactor results in the samples being decomposed into their constituents. Since no oxygen from the air is present, no combustion takes place in the conventional sense. During the decomposition of the organic samples, carbon monoxide (CO) and hydrogen ($H_2$) are normally produced. In the present case, only the CO will be considered further, initially. This is passed through a gas chromatograph (GC) 14 with a separating column, where it is separated from the other constituents. The constituents are then introduced successively into a mass spectrometer 15 (shown by dashed lines in FIG. 2), for analysis. The measurements are in this case carried out using the so-called on-line method. The various oxygen isotopes ($^{16}O$, $^{18}O$) which are present are determined directly from the detected CO molecules ($^{12}C\ ^{16}O$, $^{13}C\ ^{16}O$, $^{12}C\ ^{18}O$). An ion source, a deflection magnet, a Faraday collector with cups for the ions to be detected, and an amplifier are arranged in the mass spectrometer. The signals which are detected are evaluated by a computer.

The isotope composition of the oxygen in the sample is compared with the isotope composition of a standard gas (CO). In accordance with the method according to the invention, this standard gas is supplied in a particular form, namely as an initial product of a standard gas, in the present example as carbon dioxide ($CO_2$). The initial product is introduced into the reactor 11 from a conventional pressure cylinder 16 (10 liters at a pressure of 60 bar) via a supply line 17, a special valve 18 and the reactor supply line 12. The high temperature in the reactor 11 results in the gas being decomposed into 2CO, which represents the standard gas required for the measurement. $CO_2$ is fed into the reactor in a particular way via the valve 18, and this will be explained in more detail in the following text.

Figure 3:
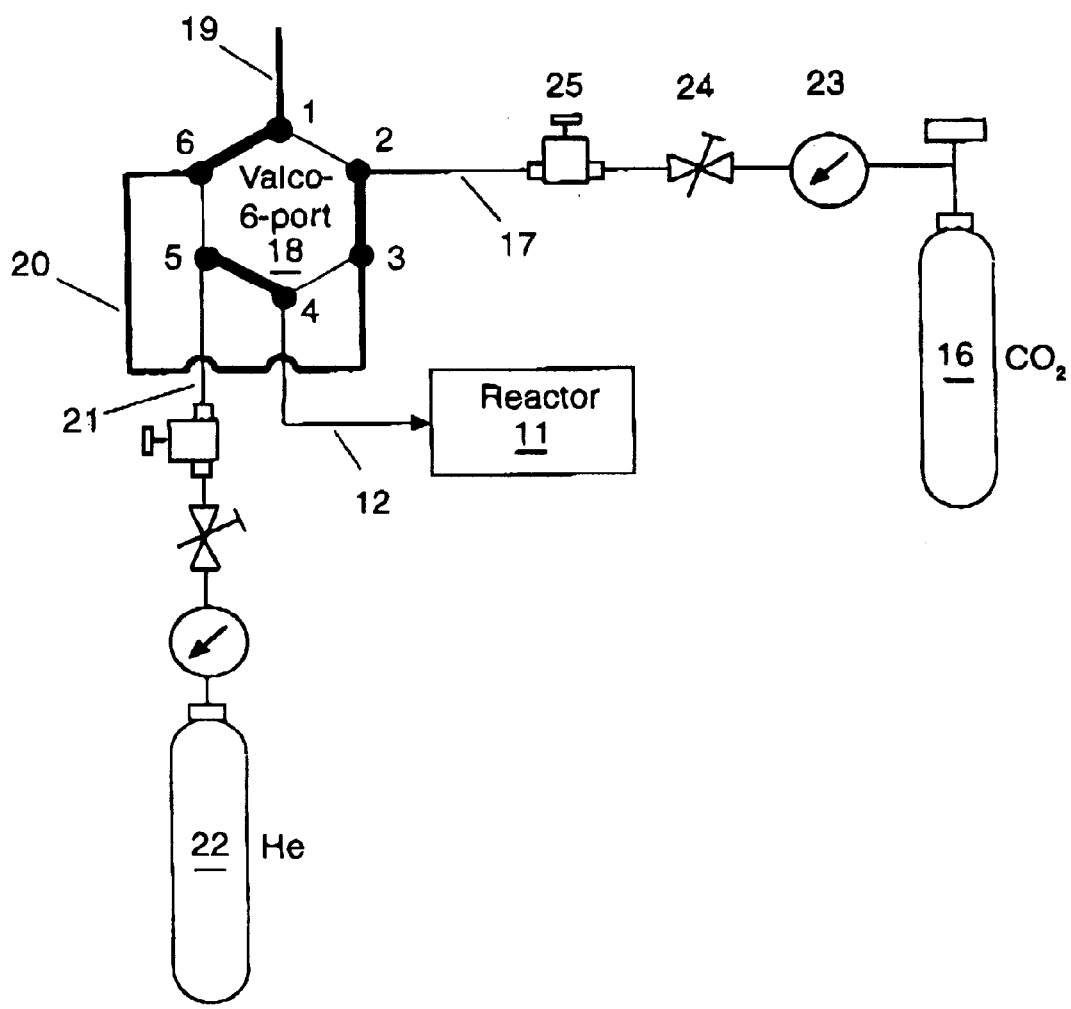
FIG. 3 shows a schematic illustration of a detail from FIG. 2 in a so-called loading position.

The valve 18 is a rotary valve, such as is available from Valco Instruments Co. Inc. (Houston, Tex.), having a total of six connection points 1 to 6, see FIGS. 3 and 4. The connection points follow one another in the form of a ring and can be connected to one another in pairs, so that a gas which enters the valve via one connection point can emerge again via the respectively closest connection point. The special feature of the valve is that a connection can alternatively be produced to the respective other adjacent connection point by means of a brief switching process. Thus, as shown in FIG. 3, the connection point 2 is connected to the connection point 3, the connection point 4 is connected to the connection point 5 and the connection point 6 is connected to the connection point 1. After switching the valve 18 over, this results in the constellation shown in FIG. 4, namely with a connection between the connection points 2 and 1, 3 and 4, and 5 and 6.

The connection points are numbered successively in the clockwise direction. The supply line 17 is connected to the connection point 2, and the reactor supply line 12 is connected to the supply line 4. A waste line 19 is connected to the connection point 1. The connection points 3 and 6 are connected to one another via a storage line 20 (loop). A helium supply 22 is, finally, connected to the connection point 5 via a carrier gas line 21.

The described apparatus is now used to provide the standard gas, as follows:

The illustration in FIG. 3 describes the so-called loading position (rest position). In this case, $CO_2$ flows out of the pressure cylinder 16 via a manometer 23, reducing valves 24 and a pressure regulator 25 together with the supply line 17 via the connection points 2 and 3 into the storage line 20 and, from there, further via the connection points 6 and 1 into the waste line 19 before flowing into free space. The storage line 20 has a volume of about 0.2 ml. The pressure regulator 25 is set such that approximately 2 to 3 ml of $CO_2$ pass through the said lines per minute. The lines connected through which the flow passes between the connection points are shown as bold lines, while the lines through which the flow cannot pass are rather thin, see between the points 1–2, 3–4, 5–6.

In parallel with the $CO_2$, helium flows as a carrier gas from the supply 22 via the valve 18 (connection points 5, 4 and lines 21, 12) into the reactor 11. In this phase, the carrier gas ensures that the constituents formed by decomposition in the reactor (from the samples from the auto sampler) are transported into the gas chromatograph 14, and then into the mass spectrometer 15.

Figure 4:
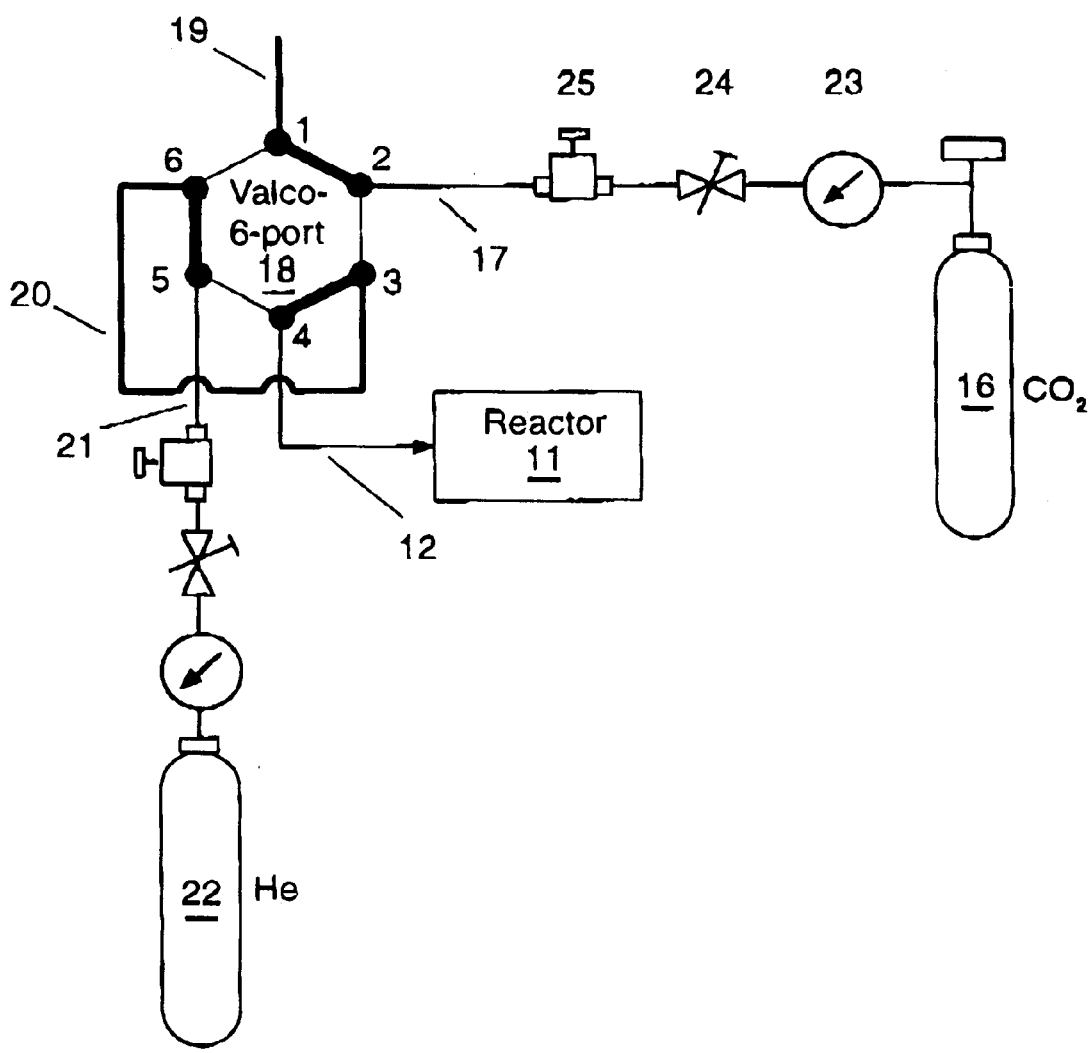
FIG. 4 shows an illustration as shown in FIG. 3 in a so-called injection position.

In order to measure the isotope composition of the standard gases, the valve 18 is switched to the position shown in FIG. 4 (injection position). Only the connection points 1 and 2, 3 and 4, and 5 and 6 are then respectively connected to one another, with these lines now being shown as bold lines. $CO_2$ flows in a corresponding manner out of the pressure cylinder 16 directly into the waste line 19. The volume Of $CO_2$ in the storage line 20 is now connected to the carrier gas line 21 and is conveyed by the helium flowing out into the reactor supply line 12, and thus into the reactor 11. There, $CO_2$ is decomposed into two 2CO [sic] and is available at the output of the reactor as standard gas for determining the isotope composition of oxygen. Thus, using the method and the apparatus according to the invention, the highly-toxic CO provided as the standard gas in the past can be replaced by the initial product $CO_2$. Furthermore, the standard gas is now formed at the same point as the sample gas, so that the measurement results are subject to less fluctuation than was normal in the past.

After approximately 10 seconds, the valve is switched back to the position shown in FIG. 3 (loading position). The next sample can then be inserted from the auto sampler 10 into the reactor 11, and can be decomposed there. The described cycle is repeated a number of times, with the time intervals being calculated or being determined experimentally as a function of the prevailing pressures and volumes.

In order to determine the isotope composition of hydrogen D/H, a propane gas cylinder, which is not shown, is connected to the valve 18. The propane ($2C_3H_8$) produces the decomposition product $6C+4H_2$ in the reactor. The H isotopes are detected in the mass spectrometer.

What is claimed is:

1. A method for producing a standard gas containing carbon monoxide (CO) and/or hydrogen ($H_2$) for determining the isotope relationships of oxygen and/or hydrogen in a sample during online operation comprising the steps of:

decomposing said sample in a heated reactor to produce a sample gas containing one or more of carbon monoxide (CO) and hydrogen ($H_2$);

feeding said decomposed sample gas to a mass spectrometer;

producing standard gases containing one or more of carbon monoxide (CO) and hydrogen ($H_2$) within said reactor via decomposition of one or more appropriate initial product gases that are fed to said heated reactor;

feeding said standard gases to said mass spectrometer; and determining the isotope relationships of oxygen and/or hydrogen in the sample gas by comparison to the isotope composition of oxygen and/or hydrogen in the standard gases.

2. The method of claim 1, wherein said initial product gases are one or more of carbon dioxide ($CO_2$) and n-alkanes.

3. The method of claim 2, wherein said n-alkanes are propane or butane.

4. An apparatus for producing standard gases for determining the isotope relationships of oxygen and/or hydrogen in a sample during online operation comprising:
- a heated reactor wherein said sample is decomposed to produce a sample gas containing one or more of carbon monoxide (CO) and hydrogen ($H_2$) and one or more initial product gases are also decomposed to produce said standard gases containing one or more of carbon monoxide (CO) and hydrogen ($H_2$);
- a mass spectrometer into which said sample gas and said standard gases are fed; and
- means for feeding said sample and said initial products product gases into said heated reactor.

5. The apparatus of claim 4, wherein said means is a line system comprising:
- a connection for at least one of said initial product gases;
- a connection to a carrier gas supply that provides a carrier gas;
- a line leading to said reactor;
- a storage line; and
- a switching means for periodically feeding said initial product gases into said storage line and for likewise periodically allowing flow of said carrier gas from said carrier gas supply to sweep the contents of said storage line into said heated reactor.

6. An apparatus according to claim 5, wherein said switching means is a rotary valve with at least six connections.

* * * * *